United States Patent [19]

Szczepanski

[11] Patent Number: 5,795,901
[45] Date of Patent: Aug. 18, 1998

[54] INSECTICIDAL N-(SUBSTITUTED ARYLMETHYL)-4-[BIS(SUBSTITUTED ARYL)HYDROXYMETHYL]PIPERIDINIUM SALTS

[75] Inventor: Steven W. Szczepanski, Morrisville, Pa.

[73] Assignee: FMC Corporation, Phila., Pa.

[21] Appl. No.: 852,160

[22] Filed: May 6, 1997

Related U.S. Application Data

[60] Provisional application No. 60/021,139, Jul. 2, 1996.
[51] Int. Cl.$^6$ .................... C07D 211/22; A01N 43/40
[52] U.S. Cl. .................... 514/326; 514/317; 514/318; 514/269; 544/335; 546/194; 546/210; 546/240
[58] Field of Search .................... 546/240, 194, 546/210; 544/335; 514/269, 317, 318, 326

[56] References Cited

U.S. PATENT DOCUMENTS

| | | | |
|---|---|---|---|
| 5,569,664 | 10/1996 | Silverman et al. | 514/317 |
| 5,639,763 | 6/1997 | Silverman et al. | 514/319 |

*Primary Examiner*—Bernard Dentz

[57] ABSTRACT

Compounds of the following structure are disclosed as effective insecticides:

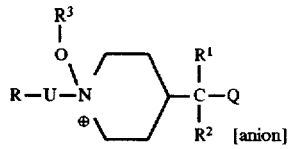

in which Q is hydroxy; U is —$(CH_2)_n$—, where n is 1; R is

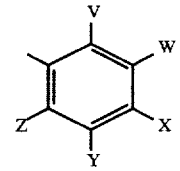

in which V, W, Y, and Z are each hydrogen; X is alkoxy, cycloalkylalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl; $R^1$ and $R^2$ are independently selected from haloalkyl; phenyl substituted with halogen, halothio, haloalkyl, or haloalkoxy; or a five- or six-membered heteroaryl substituted with halogen or haloalkyl; $R^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt; and a separate anion is chloride, bromide, iodide, or an phenyl or alkyl sulfate or sulfonate; with the proviso that at least one of $R^1$ and $R^2$ is phenyl substituted in the para position or pyrid-2-yl or pyrimidin-2-yl, each substituted in the the 5-position; each aliphatic moiety contains not more than 4 carbon atoms, except that $R^3$ may contain up to eighteen carbon atoms; halogen means bromine, chlorine, or fluorine; each heteroaryl contains from 1 to 4 nitrogen atoms, or 1 or 2 oxygen or sulfur atoms, or 1 or 2 nitrogen atoms and an oxygen or sulfur atom.

27 Claims, No Drawings

INSECTICIDAL N-(SUBSTITUTED ARYLMETHYL)-4-|BIS(SUBSTITUTED ARYL)HYDROXYMETHYL|PIPERIDINIUM SALTS

This application derives priority from verified Provisional Application No. 60/021,139 filed Jul. 2, 1996.

The present invention relates to methods for controlling insects. In particular, it relates to control by the application of certain novel N-(substituted arylmethyl)-4-|bis (substituted phenyl or pyridyl)hydroxymethyl|piperidinium salts and to the locus where insect control is needed.

It is known that certain N-(substituted arylmethyl)-4-|bis (substituted aryl)-hydroxymethyl|piperidine compounds, as well as their salts and N-oxides, are effective insecticides. It has now been found that the salts of compounds of the following structure are active as insecticides:

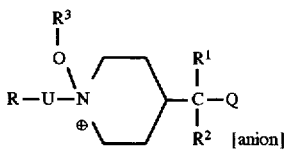

in which:

Q is hydroxy;

U is —(CH$_2$)$_n$—, where n is 1;

R is

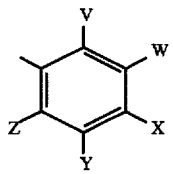

where V, W, Y, and Z are each hydrogen;

X is alkoxy, cycloalkylalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl;

R$^1$ and R$^2$ are independently selected from haloalkyl; phenyl substituted with halogen, halothio, haloalkyl, or haloalkoxy; or a five- or six-membered heteroaryl substituted with halogen or haloalkyl;

R$^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt; and a separate anion is chloride, bromide, iodide, or an phenyl or alkyl sulfate or sulfonate;

with the proviso that at least one of R$^1$ and R$^2$ is phenyl substituted in the para position or pyrid-2-yl or pyrimidin-2-yl, each substituted in the the 5-position; each aliphatic moiety contains not more than 4 carbon atoms, except that R$^3$ may contain up to eighteen carbon atoms; halogen means bromine, chlorine, or fluorine; each heteroaryl contains from 1 to 4 nitrogen atoms, or 1 or 2 oxygen or sulfur atoms, or 1 or 2 nitrogen atoms and an oxygen or sulfur atom.

Since the compounds of the invention differ from the piperidine compounds from which they are derived in chemical and physical properties, they can be formulated in ways not possible or practicable for the parent compounds. These differences can also be expected to affect the manner in which the target insects metabolize the compounds.

Preferred are those compounds in which

X is alkoxy, cycloalkylalkoxy, alkoxycarbonyl, alkoxycarbonylamino, or a five- or six-membered heteroaryl or heteroaryloxy; each heteroaryl selected from 1,2,4-oxadiazolyl, oxazolinyl, pyridazinyl, pyrazinyl, pyridyl, pyrimidinyl, pyrolyl, 2H-tetrazol-5-yl, 1,2,3-thiadiazolyl, 1,3,5-triazinyl, and 1,2,4-triazolyl, each optionally substituted with halogen, cyano, alkyl, haloalkyl, alkoxy, haloalkoxy, alkoxyalkyl, or haloalkoxyalkyl;

R$^1$ and R$^2$ are independently selected from ptrifluoromethoxyphenyl, p-trifluoromethylphenyl, 5-trifluoromethylpyrid-2-yl, and 5-trifluoromethoxypyrid-2-yl; 5-trifluoromethylpyrimidin-2-yl, and 5-trifluoromethoxypyrimidin-2-yl;

R$^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, or arylcarbonyl; and a separate anion is chloride, bromide, or iodide;

with the proviso that halogen means chlorine or fluorine, and R$^3$ may contain up to twelve carbon atoms.

Particularly preferred are those compounds in which

X is a n-propyloxy, cyclopropylmethoxy, methoxycarbonylamino, i-propoxycarbonylamino, or a heteroaryl selected from 1,2,4-oxadiazol-5-yl, oxazolin-2-yl, pyrid-2-yl, pyrimidin-2-yl, pyrol-3-yl, 2H-tetrazol-5yl, 1,2,3-thiadiazol-4-y1, 1,2,4-triazol-3-yl, each optionally substituted with halogen, cyano, C$_{(1-3)}$alkyl, C$_{(1-3)}$haloalkyl, or C$_{(1-4)}$alkoxyalkyl;

R$^3$ is alkyl, C$_{(1-4)}$haloalkyl, C$_{(1-4)}$hydroxyalkyl, C$_{(1-4)}$alkoxyalkyl, C$_{(1-4)}$dialkylaminoalkyl, C$_{(1-4)}$alkylaminocarbonyloxyalkyl, C$_{(1-4)}$alkylthioalkyl, C$_{(1-4)}$alkylcarbonyloxyalkyl, C$_{(1-4)}$alkoxycarbonylalkyl, carboxyC$_{(1-4)}$alkyl, benzylcarboxy, or benzoyl.

The compounds of the present invention were prepared by methods known to one skilled in the art. In one method, as depicted in Schema 1, ethyl piperidin-4-ylcarboxylate was reacted with an appropriately substituted phenylalkyl halide, for example, 4-propoxyphenylmethyl chloride, affording the corresponding ethyl N-substituted alkylpiperidin-4-ylcarboxylate (A). The so-prepared ethyl carboxylate (A) was then treated with a two to three molar excess of the Grignard reagent of an appropriately substituted halide, for example, 4-trifluoromethylphenyl magnesium bromide, yielding the intermediate N-(substituted alkyl)-4-|bis (substituted)hydroxy-methyl|piperidine (I). The N-oxides (IA) were prepared by treating (I) with an oxidizing agent, such as 30% aqueous hydrogen peroxide or 50% 3-chloroperoxybenzoic acid in an appropriate solvent, yielding the corresponding N-oxide, for example, N-(4-propoxyphenylmethyl)-4- |bis(trifluoromethylphenyl) hydroxy-methyl|piperidine N-oxide. The N-oxide (IA) was then reacted with an appropriate halide such as ethyl iodide or 3-bromopropionic acid, or a sulfate or sulfonate, as shown in Schema 3, yielding the targeted salts.

In an alternative method, ethyl piperidin-4-ylcarboxylate was reacted with trimethylsilyl chloride, yielding ethyl N-trimethylsilylpiperidin-4-ylcarboxylate (B). Intermediate (B) was then reacted with a two to three molar excess of the Grignard reagent of an appropriately substituted halide, as described above, affording a 4-[bis(substituted) hydroxymethyl]piperidine (C), for example 4-[bis(4-trifluoromethylphenyl)hydroxymethyl]piperidine. Intermediate (C) was reacted with an appropriately substituted phenylalkyl halide, as described above, yielding the corresponding intermediate N-(substituted alkyl)-4-[bis(substituted)hydroxymethyl]piperidine (I). The N-oxide of (I) and the targeted salts and betaines were prepared as describes above.

Schemata 1–3 depict the general methods used to prepare these compounds. Examples 1 and 2 provide the details for these methods of preparation.

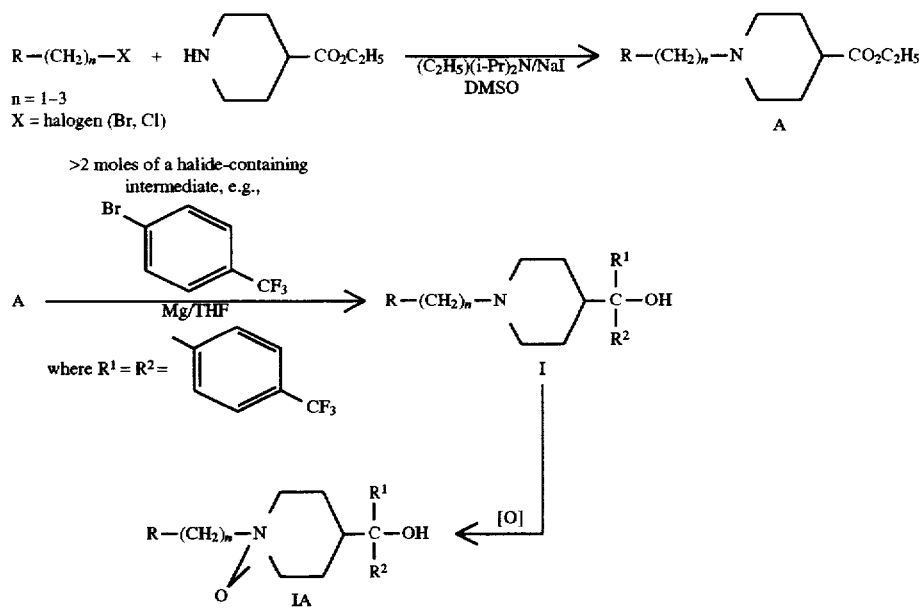

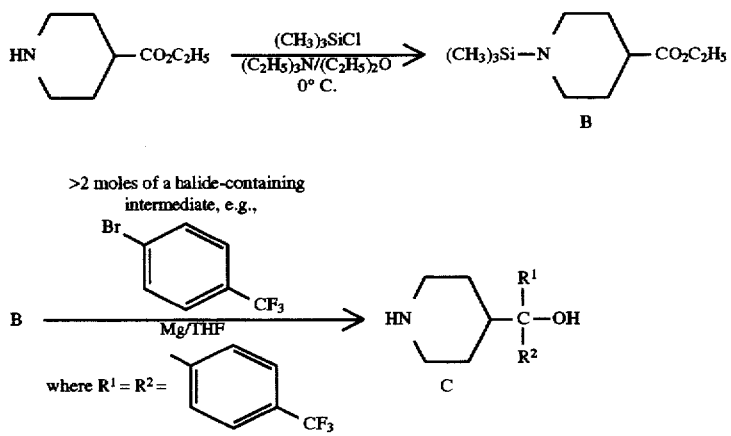

-continued
SCHEMA 2

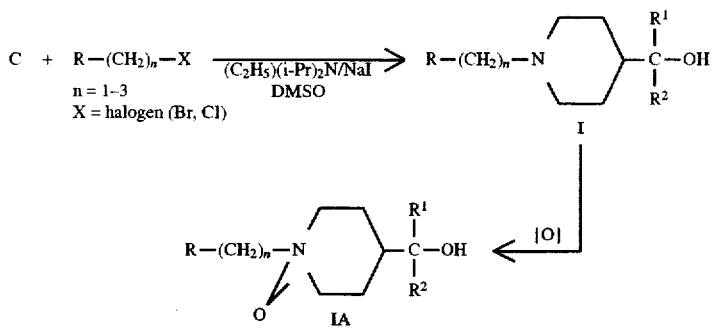

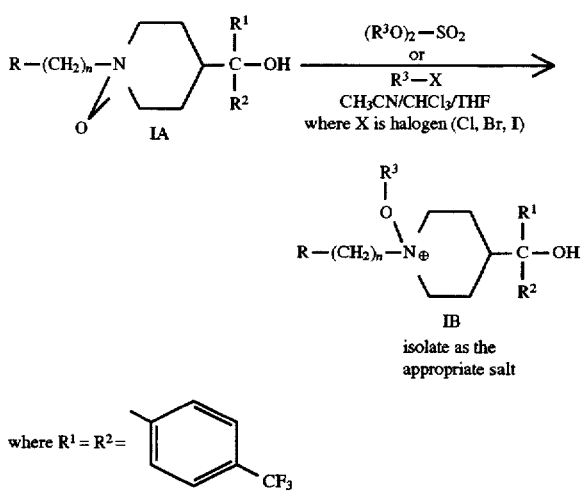

where $R^1 = R^2 = $ [4-CF$_3$-phenyl]

EXAMPLE 1

SYNTHESIS OF N-(4-PROPOXYPHENYLMETHYL)-N-(2-CARBOXYETHOXY)-4-[BIS(4-TRIFLUOROMETHYLPHENYL) HYDROXYMETHYL]PIPERIDINIUM INNER SALT (COMPOUND 6)

Step A Synthesis of 4-propoxyphenylmethyl chloride as an intermediate

A mixture of 53.8 grams (0.33 mole) of 4-propoxybenzaldehyde, 200 mL of ethanol, and 200 mL of tetrahydrofuran was stirred, and 3.3 grams (0.09 mole) of sodium borohydride was added portionwise during a 30 minute period. The reaction caused the reaction mixture temperature to rise to about 45° C. Upon completion of the addition the reaction mixture was stirred for one hour and poured into 500 mL of water containing 50 grams of ammonium chloride. The mixture was then extracted with two 500 mL portions of diethyl ether. The combined extracts were washed with one 500 mL portion of an aqueous solution saturated with sodium chloride. The organic layer was dried with magnesium sulfate and filtered. The filtrate was concentrated under reduced pressure, yielding 53.6 grams of white solid. The solid was dissolved in 75 mL of methylene chloride and 0.75 mL of pyridine was added. The solution was added dropwise to a cold (10° C.), stirred solution of 28 mL (0.38 mole) of thionyl chloride in 350 mL of methylene chloride. The complete addition required one hour, during which time the reaction mixture was maintained at 10° C. Upon completion of the addition the reaction mixture was stirred for one hour and poured into a addition the reaction mixture was stirred for one hour and poured into a solution of 350 mL of water containing 100 mL of an aqueous solution saturated with ammonium chloride. The organic layer was washed with two 250 mL portions of an aqueous solution saturated with sodium bicarbonate, and dried with magnesium chloride. The mixture was filtered, and the filtrate was concentrated under reduced pressure, yielding 56.4 grams of material. The material was distilled under reduced pressure, yielding 52.5 grams of 4-propoxyphenylmethyl chloride, bp 92° C./0.3 mm Hg.

Step B Synthesis of ethyl N-(4-propoxyphenylmethyl) piperidin-4-yl carboxylate as an intermediate A solution of 47.5 grams (0.30 mole) of ethyl piperidin-4-ylcarboxylate in 70 mL (0.40 mole) of N,N-diisopropylethylamine was stirred, and a solution of 52.5 grams (0.29 mole) of 4-propoxyphenylmethyl chloride in 50 mL of dimethyl sulfoxide was added dropwise. The reaction caused the reaction mixture temperature to rise to about 35° C. Upon completion of the addition the reaction mixture was stirred for 30 minutes, warmed to 40° C., and then allowed to cool to ambient temperature. After this time the reaction mixture was poured into 500 mL of aqueous 10% ammonium chloride. The mixture was extracted with three 250 mL portions of diethyl ether, and the combined extracts were washed with two 250 mL portions of an aqueous solution saturated with ammonium chloride, one 250 mL portion of water, and one 250 mL portion of an aqueous solution saturated with sodium chloride. The organic layer was dried with magnesium sulfate and filtered. The filtrate was concentrated under reduced pressure, yielding 80.0 grams of ethyl N-(4-propoxyphenylmethyl)-piperidin-4-ylcarboxylate. The NMR spectrum was consistent with the proposed structure:

Step C Synthesis of N-(4-propoxyphenylmethyl)-4-[bis (trifluoromethylphenyl)hydroxymethyl]piperidine as an intermediate A mixture of 0.4 gram (0.015 gram-atom) of magnesium turnings in 10 mL of tetrahydrofuran was placed in a reaction vessel which was then purged with nitrogen. To this was added 0.25 mL of 4-trifluoromethylphenyl bromide. The stirred mixture was warmed to reflux, and a solution of 1.85 mL (0.015 mole total) and 1.5 grams (0.005 mole) of ethyl N-(4-propoxyphenylmethyl)piperidin-4-ylcarboxylate in 5 mL of tetrahydrofuran was added dropwise during a 30 minute period. Upon completion of the addition, the reaction mixture was heated at reflux for an additional one hour, then cooled to ambient temperature and poured into an aqueous solution saturated with ammonium chloride. The mixture was extracted with ethyl acetate, and the extract was dried with magnesium sulfate. The mixture was filtered, and the filtrate was concentrated under reduced pressure, yielding a crude product that was subjected to column chromatography on silica gel with 1:1 ethyl acetate: heptane as the eluant. The product-containing fractions were combined and concentrated under reduced pressure, yielding 1.4 grams of N-(4-propoxyphenylmethyl)-4-[bis-(trifluoromethylphenyl) hydroxymethyl]piperidine. The NMR spectrum was consistent with the proposed structure.

Step D Synthesis of N-(4-propoxyphenylmethyl)-4-[bis(4-trifluoro methylphenyl)-hydroxymethyl]piperidine N-oxide as an intermediate To a stirred solution of 1.5 grams (0.003 mole) of N-(4-propoxyphenylmethyl)-4-[bis(4-trifluoromethylphenyl) hydroxymethyl]piperidine in 25.0 mL of absolute methanol was added 1.4 mL (0.014 mole) of 30% aqueous hydrogen peroxide in one portion. Upon completion of the addition the reaction mixture was stirred at ambient temperature for five hours and then analyzed by thin layer chromatography (TLC), which indicated the reaction was not complete. An additional 3.0 mL (0.029 mole) of 30% aqueous hydrogen peroxide was added, and the reaction mixture was stirred for about 18 hours. At the conclusion of this period the reaction mixture was poured into 100 mL of an aqueous saturated sodium chloride solution. The mixture was extracted with three 100 mL portions of ethyl acetate, and the combined extracts were washed with one 100 mL portion of an aqueous saturated sodium chloride solution. The organic layer was dried with sodium sulfate and filtered. The filtrate was concentrated under reduced pressure, yielding 1.5 grams of N-(4-propoxyphenylmethyl)-4-[bis(4-trifluoromethylphenyl)hydroxymethyl]piperidine N-oxide. The NMR spectrum was consistent with the proposed structure.

Step E Synthesis of N-(4-propoxyphenylmethyl)-N-(2-carboxyethoxy)-4-[bis(4-trifluoromethylphenyl) hydroxymethyl]piperidinium inner salt (Compound 6)

Under a nitrogen atmosphere, a solution of 1.1 grams (0.002 mole) of N-(4-propoxyphenylmethyl)-4-[bis(4-trifluoromethylphenyl)hydroxymethyl]piperidine N-oxide, 0.3 gram (0.002 mole) of 3-bromopropionic acid, and a 1:1 mixture of acetonitrile and chloroform was stirred at ambient temperature for about 48 hours. The reaction mixture was then filtered, and the filtrate was concentrated under reduced pressure, yielding 0.5 gram of N-(4-propoxyphenyl-methyl)-N-(2-carboxyethoxy)-4-[bis(4-trifluoromethylphenyl)hydroxymethyl]-piperidinium inner salt. The NMR spectrum was consistent with the proposed structure.

EXAMPLE 2

SYNTHESIS OF N-[4-(CYCLOPROPYLMETHOXY)PHENYLMETHYL]-N-ETHOXY-4-[BIS(4-TRIFLUOROMETHYLPHENYL)HYDROXY-METHYL]PIPERIDINIUM IODIDE (COMPOUND 11)

Step A Synthesis of ethyl N-trimethylsilylpiperidin-4-ylcarboxylate

Under a nitrogen atmosphere a stirred solution of 50.0 grams (0.313 mole) of ethyl piperidin-4-ylcarboxylate in 300 mL of diethyl ether was cooled to 0° C. and 33.8 grams (0.338 mole) of triethylamine was added in one portion. To this was added dropwise during a 30 minute period a solution of 34.6 grams (0.338 mole) of trimethylsilyl chloride in 100 mL of diethyl ether. Upon completion of the addition the reaction mixture was stirred for five hours, then it was filtered to remove triethylamine hydrochloride. The filtrate was concentrated under reduced pressure to a residue. The residue was then dissolved in 200 mL of hexane in which it was allowed to stand for about two hours under a nitrogen atmosphere. The solution was filtered and concentrated under reduced pressure, yielding 66.9 grams of ethyl N-trimethylsilylpiperidin-4-ylcarboxylate. The NMR spectrum was consistent with the proposed structure.

Step B Synthesis of 4-[bis(4-trifluoromethylphenyl) hydroxymethyl]piperidine as an intermediate This compound was prepared in the manner of Step C of Example 1, with 30 grams (0.131 mole) of ethyl N-trimethylsilylpiperidin-4-ylcarboxylate, 70.6 grams (0.314 mole) of 4-trifluoromethylphenyl bromide, and 7.8 grams (0.320 gram-atom) of magnesium turnings in about 400 mL of tetrahydrofuran as reagents. The yield of 4-[bis (4-trifluoromethylphenyl)hydroxymethyl]piperidine was 33.0 grams of powdery solid. The NMR spectrum was consistent with the proposed structure.

Step C Synthesis of N-[4-(cyclopropylmethoxy) phenylmethyl]-4-[bis(4-trifluoromethylphenyl) hydroxymethyl]piperidine as an intermediate A solution of 20.5 grams (0.051 mole) of 4-[bis(4-trifluoromethylphenyl)hydroxymethyl]piperidine, 10.0 grams (0.051 mole) of 4-(cyclopropylmeth-oxy) phenylmethyl chloride (prepared as in Step A of Example 1), and 35.4 mL (0.203 mole) of N,N'-diisopropylethylamine in 200 mL of dimethyl sulfoxide was stirred at ambient temperature for about 18 hours. The reaction mixture was then poured into an aqueous solution saturated with sodium bicarbonate. The mixture was extracted with two portions of ethyl acetate, and the extracts combined. The combination was dried with sodium sulfate and filtered. The filtrate was concentrated under reduced pressure to a residue, which was subjected to column chromatography on silica gel with 50% heptane in methylene chloride to 50% acetone in methylene chloride. The product-containing fractions were combined and concentrated under reduced pressure, yielding 22.0 grams of N-[4-(cyclopropylmethoxy)phenylmethyl]-4-[bis (4-trifluoromethylphenyl)hydroxymethyl]piperidine. The NMR spectrum was consistent with the proposed structure.

Step D Synthesis of N-[4-(cyclopropylmethoxy) phenylmethyl]-4-[bis(4-trifluoromethylphenyl) hydroxymethyl]piperidine N-oxide as an intermediate A stirred solution of 10.0 grams (0.018 mole) of N-[4-(cyclopropylmethoxy)phenylmethyl]-4-[bis(4-trifluoromethylphenyl)hydroxymethyl]piperidine in methylene chloride was cooled to 0° C., and 3.1 grams (0.01 2 mole) of 50% 3-chloroperoxybenzoic acid was added in two portions. Upon completion of the addition the reaction mixture was allowed to warm to ambient temperature, where it stirred for about 18 hours. After this time, the reaction mixture was poured into aqueous 5% sodium hydroxide solution. The organic layer was separated and washed with aqueous 5% sodium hydroxide solution. The organic layer was then filtered through phase separated silicone treated paper. The filtrate was concentrated under reduced pressure, yielding 10.2 grams of N-[4-(cyclopropylmethoxy) phenylmethyl]-4-[bis(4-trifluoromethylphenyl)hydroxymethyl]piperidine N-oxide. The NMR spectrum was consistent with the proposed structure.

Step E Synthesis of N-[4-(cyclopropylmethoxy) phenylmethyl]-N-ethoxy-4-[bis(4-trifluoromethylphenyl) hydroxymethyl]piperidinium iodide (Compound 11)

A stirred mixture of 1.0 gram (0.002 mole) of N-[4-(cyclopropylmethoxy)phenylmethyl]-4-[bis(4-trifluoromethylphenyl)hydroxy-methyl]piperidine N-oxide, 0.3 gram (0.002 mole) of ethyl iodide, and about 5.0 mL of acetonitrile was heated at reflux for several hours. The reaction mixture was then cooled to 0° C., and petroleum ether was added. Upon completion of the addition the mixture was filtered and the filtrate was concentrated under reduced pressure, yielding 0.6 gram of N-[4-(cyclopropylmethoxy)phenylmethyl]-N-ethoxy-4-[bis(4-trifluoromethylphenyl)hydroxymethyl]-piperidinium iodide. The NMR spectrum was consistent with the proposed structure.

Representative compounds prepared by the methods exemplified above are listed in Table 1. Characterizing properties are given in Table 2.

Biological Data

Candidate insecticides were incorporated into an artificial diet for evaluation of insecticidal activity against the tobacco budworm (*Heliothis virescens* [Fabricius]) in the following manner. Stock solutions of test chemical in dimethyl sulfoxide, ranging from 50 micromolar to 0.005 micromolar, were prepared for each rate of application. One hundred microliters of each of the stock solutions was manually stirred into 50 mL of a molten (65°–70° C.) wheat germ-based artificial diet. The 50 mL of molten diet containing the test chemical was poured evenly into twenty wells in the outer two rows on each side of a twenty-five well, five row plastic tray. (Each well in the tray was about 1 cm in depth, with an opening of 3 cm by 4 cm at the lip.) Molten diet containing only dimethyl sulfoxide at the levels used in the test chemical-treated diet was poured into the five wells in the third (center) row of the tray. Each tray therefore contained one test chemical at a single rate of application, together with an untreated control. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

Single second instar tobacco budworm larvae, selected at a stage of growth at which they uniformly weigh about 5 mg each, were placed in each well. Upon completion of infestation, a sheet of clear plastic was heat-sealed over the top of the tray by use of a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Also, where possible, the negative log of the concentration of the test chemical that provided 50% mortality ($pLC_{50}$) was determined.

Candidate insecticides with high $pI_{50}$ values from the diet test were tested for insecticidal activity in foliar evaluations against tobacco budworm, beet armyworm (*Spodoptera exigua* [Hubner]), and cabbage looper (*Trichoplusia ni* [Hubner]).

In these tests against tobacco budworm and beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing one chick pea plant, for each rate of application of test chemical were sprayed. The treated plants were transferred to a hood, where they were kept until the spray had dried.

The four chick pea plants for each replicate treated with test chemical as described above were removed from their pots by cutting the stems just above the soil line. The excised leaves and stems from the four plants in each replicate were placed in individual 8-ounce paper cups, each containing a moistened filter paper. Five second-instar (6 days old) tobacco budworms or beet armyworms (7–8 days old) were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead, moribund, and live insects were counted. Using the insect counts, the efficacy of the test chemical was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Foliar tests with cabbage looper were conducted in the same manner as described above, the difference being that pinto bean plants (*Phaseolus vulgaris*) were used in place of chick pea plants.

The compounds of the present invention were active in the diet test against the tobacco budworm. Table 3 gives the insecticidal activity data for compounds tested in the diet test.

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined inventive concepts herein as defined in the claims.

TABLE 1

Insecticidal N-(substituted alkyl)-4-[di(substituted)hydroxymethyl]piperidinium Salts

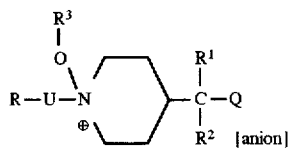

Where U is $-(CH_2)_n-$; n is 1; Q is $-OH$; and R is

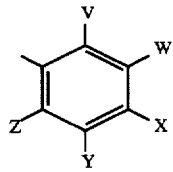

wherein V, W, Y, and Z are hydrogen

| Cmpd. No | X | R¹ | R² | R³* | Anion |
|---|---|---|---|---|---|
| 1 | 2-pyridyloxy | A | C | ~~S~CH₃ (propyl thiomethyl) | chloride |
| 2 | 1-(2-fluoroethyl)-tetrazol-3-yl | A | D | ~~O-C(=O)-CH₃ (propyl acetate) | bromide |
| 3 | 1-(2-fluoroethyl)-tetrazol-3-yl | A | G | ~~~O-C(=O)-CH₃ (butyl acetate) | bromide |
| 4 | 1-(2-fluoroethyl)-tetrazol-3-yl | A | H | ~~O-C(=O)-NHCH₃ | chloride |
| 5 | -OCH₂CH₃ (ethoxy) | B | B | -CH₃ | iodide |
| 6 | -OCH₂CH₃ | C | C | ~~~C(=O)O⁻ | inner salt |
| 7 | -OCH₂-cyclopropyl | C | C | ~~C(=O)O⁻ | inner salt |
| 8 | -OCH₂-cyclopropyl | C | C | ~~~C(=O)O⁻ | inner salt |
| 9 | -OCH₂-cyclopropyl | C | C | ~~~~C(=O)O⁻ | inner salt |
| 10 | -OCH₂-cyclopropyl | C | C | ~~~C(=O)O-CH₃ | bromide |
| 11 | -OCH₂-cyclopropyl | C | C | $-C_2H_5$ | iodide |
| 12 | -OCH₂-cyclopropyl | C | C | $-C_3H_7$ | iodide |

TABLE 1-continued

| # | R₁ | | | R₂ | Counterion |
|---|----|----|----|----|------------|
| 13 | OCH₂-cyclopropyl | C | C | —C₁₂H₂₅ | bromide |
| 14 | OCH₂-cyclopropyl | C | C | —CH₃ | methyl sulfate salt |
| 15 | OCH₂-cyclopropyl | C | C | —CH₂C(O)C₆H₅ (phenacyl) | chloride |
| 16 | OCH₂-cyclopropyl | C | C | —(CH₂)₄C(O)O⁻ | inner salt |
| 17 | OCH₂-cyclopropyl | C | C | —(CH₂)₃S(O)₂O⁻ | inner salt |
| 18 | OCH₂-cyclopropyl | C | C | —CH₂S(O)₂O⁻ | inner salt |
| 19 | OCH₂-cyclopropyl | C | C | —CH₂CH(CH₃)C(O)O⁻ (from ethyl group shown) / CH(C₂H₅)(CH₃)C(O)O⁻ | inner salt |
| 20 | OCH₂-cyclopropyl | C | C | —CH(C₂H₅)₂C(O)O⁻ | inner salt |
| 21 | OCH₂-cyclopropyl | C | C | —CH(C₂H₅)(C₆H₅)C(O)O⁻ | inner salt |
| 22 | CH₃C(O)OCH₂CH₃ | C | C | —CH₂CH₂C(O)O⁻ | inner salt |
| 23 | CH₃C(O)OCH(CH₃)₂ | C | C | —(CH₂)₃C(O)OCH₂CH₃ | bromide |
| 24 | CH₃NHC(O)OCH₃ | C | C | —(CH₂)₃S(O)₂CH₃ | chloride |
| 25 | CH₃NHC(O)OCH(CH₃)₂ | C | C | —(CH₂)₃N(CH₃)₂ | chloride |
| 26 | 1,5-dimethyltetrazolyl | C | C | —(CH₂)₃C(O)O⁻ | inner salt |

TABLE 1-continued
| # | R1 | Col1 | Col2 | R2 | Counterion |
|---|---|---|---|---|---|
| 27 | 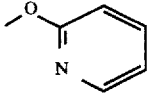 | C | C | —C₃H₆F | bromide |
| 28 | 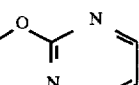 | C | C | 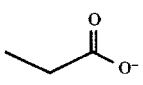 | inner salt |
| 29 | 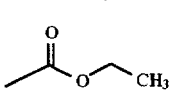 | D | D | 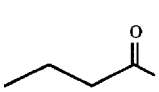 | bromide |
| 30 | 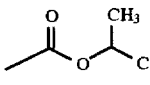 | D | D | 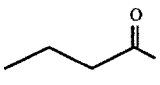 | inner salt e |
| 31 | 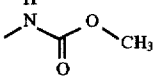 | D | D | 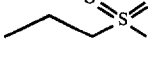 | chloride |
| 32 | 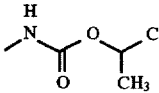 | D | D | 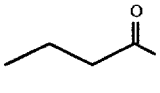 | inner salt |
| 33 | 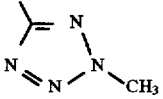 | D | D | 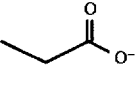 | inner salt |
| 34 | 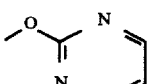 | D | D | 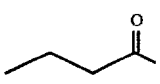 | bromide |
| 35 | 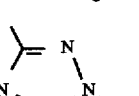 | E | E | 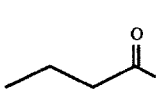 | bromide |
| 36 | 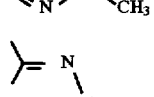 | F | C | —C₂H₄OH | chloride |
| 37 | 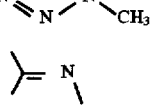 | G | C |  | bromide |
| 38 | 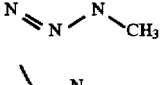 | G | G | —C₂H₄OCH₃ | bromide |
| 39 | 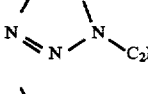 | H | C | —C₃H₆OH | chloride |
| 40 | 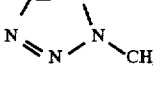 | C | C |  | bromide |
| 41 | 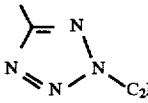 | C | C | 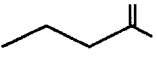 | bromide |

TABLE 1-continued
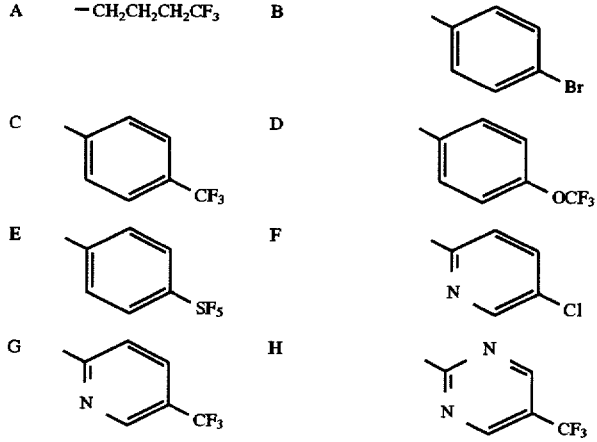
wherein $R^1$ and $R^2$ are selected from:
- A  $-CH_2CH_2CH_2CF_3$
- B  4-bromophenyl
- C  4-(trifluoromethyl)phenyl
- D  4-(trifluoromethoxy)phenyl
- E  4-(pentafluorosulfanyl)phenyl
- F  6-chloropyridin-3-yl (2-methyl, 5-Cl pyridine)
- G  5-(trifluoromethyl)pyridin-2-yl
- H  5-(trifluoromethyl)pyrimidin-2-yl
*$R^3$ attaches to the oxygen at the left position.

TABLE 2

Characterization Data

| Compound Number | Melting Point (°C)/ Physical State |
|---|---|
| 5 | 140 dec |
| 6 | 128–130 |
| 7 | 107–108 |
| 8 | SOLID |
| 9 | 62–63 |
| 10 | SOLID |
| 11 | SOLID |
| 12 | TAN SOLID |
| 13 | GUM |
| 14 | GREY SOLID |
| 15 | GLASSY SOLID |
| 16 | 95–96 |
| 23 | 160–165 |
| 40 | 164–166 |
| 41 | 120 |
| 42 | SOLID |
| 43 | 189–191 |
| 44 | 187–188 |
| 45 | 185–187 |
| 46 | 178–180 |
| 47 | 110–120 DEC |
| 48 | 95–100 |
| 49 | 150–160 |
| 50 | 80–85 DEC |
| 51 | 95–105 |

TABLE 3

Insecticidal Activity of N-(substituted arylmethyl)-4-[bis(substituted aryl)hydroxymethyl]piperidinium Salts Incorporated into the Diet of Tobacco Budworm

| Cmpd No. | Rate of Appln.[1] | Percent Growth Inhibition[2] | $pL_{50}$[3] | Percent Mortality[4] | $pL_{50}$[5] |
|---|---|---|---|---|---|
| 5 | 4 | 99 | 5.5 | 65 | 4.2 |
| 6 | 4 | 100 | 6.5 | 100 | 5.6 |
| 7 | 4 | 100 | 6.5 | 100 | 5.5 |
| 8 | 4 | 100 | 6.5 | 100 | 5.9 |
| 10 | 4 | 100 | 6.5 | 100 | 5.8 |
| 11 | 4 | 100 | 6.5 | 100 | 5.5 |
| 12 | 4 | 100 | 6.2 | 100 | 5.5 |
| 13 | 4 | 100 | 6.4 | 100 | 5.6 |
| 14 | 4 | 100 | 6.1 | 100 | 5.5 |
| 15 | 4 | 100 | 5.6 | 100 | 5.0 |
| 23 | 4 | 100 | 6.5 | 100 | 6.1 |
| 40 | 4 | 100 | 6.7 | 100 | 6.5 |
| 41 | 4 | 100 | 6.6 | 100 | 6.4 |
| 42 | 4 | 100 | 6.5 | 100 | 6.0 |
| 43 | 4 | 100 | 6.5 | 100 | 6.1 |
| 44 | 4 | 100 | 6.4 | 100 | 6.0 |
| 45 | 4 | 20 | — | 0 | — |
| 46 | 4 | 100 | 6.2 | 100 | 4.9 |
| 47 | 4 | 100 | 5.5 | 100 | 5.1 |
| 48 | 4 | 87 | 4.5 | 30 | <4.0 |
| 49 | 4 | 100 | 6.1 | 100 | 5.6 |
| 50 | 4 | 100 | 5.6 | 100 | 5.5 |
| 51 | 4 | 100 | 5.6 | 100 | 5.5 |

[1] The rate of application is expressed as the negative log of the molar concentration of the test compound in the diet.
[2] Percent growth inhibition is derived from the total weight of the insects (TW) at each rate of application in the test relative to the total weight of the insects in an untreated control:

% Gr. Inh = $\frac{|TW (control) - TW (test)|}{|TW (control)|} \times 100$

[3] $pL_{50}$ is the negative log of the concentration of the test chemical that provides 50% growth inhibition in the test species.
[4] Percent mortality is derived from the number of dead insects (TD) relative to the number of insects (TI) used in the test.

% Mortality = $\frac{TD}{TI} \times 100$

[5] $pL_{50}$ is the negative log of the concentration of the test chemical that provides 50% mortality of the test insects.

I claim:
1. A compound of the formula:

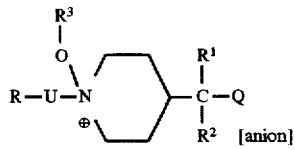

in which
Q is hydroxy;
U is —$(CH_2)_n$—, where n is 1;
R is

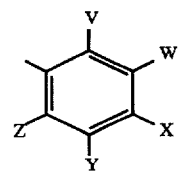

in which:
V, W, Y, and Z are each hydrogen;
X is alkoxy, cycloalkylalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl;
$R^1$ and $R^2$ are independently selected from haloalkyl; phenyl substituted with halogen, halothio, haloalkyl, or haloalkoxy; or a five- or six-membered heteroaryl substituted with halogen or haloalkyl;
$R^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt; and
a separate anion is chloride, bromide, iodide, or an phenyl or alkyl sulfate or sulfonate;

with the proviso that at least one of $R^1$ and $R^2$ is phenyl substituted in the para position or pyrid-2-yl or pyrimidin-2-yl, each substituted in the the 5-position; each aliphatic moiety contains not more than 4 carbon atoms, except that $R^3$ may contain up to eighteen carbon atoms; halogen means bromine, chlorine, or fluorine; each heteroaryl contains from 1 to 4 nitrogen atoms, or 1 or 2 oxygen or sulfur atoms, or 1 or 2 nitrogen atoms and an oxygen or sulfur atom.

2. A compound of claim 1 in which

X is a heteroaryl or heteroaryloxy; each heteroaryl selected from 1,2,4-oxadiazolyl, oxazolinyl, pyridazinyl, pyrazinyl, pyridyl, pyrimidinyl, pyrolyl, 2H-tetrazol-5-yl, 1,2,3-thiadiazolyl, 1,3,5-triazinyl, and 1,2,4-triazolyl, each optionally substituted with halogen, cyano, alkyl, haloalkyl, alkoxy, haloalkoxy, alkoxyalkyl, or haloalkoxyalkyl;

$R^1$ and $R^2$ are independently selected from ptrifluoromethoxyphenyl, p-trifluoromethylphenyl, 5-trifluoromethylpyrid-2-yl, and 5-trifluoromethoxypyrid-2-yl; 5-trifluoromethylpyrimidin-2-yl, and 5-trifluoromethoxypyrimidin-2-yl;

$R^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, or arylcarbonyl; and a separate anion is chloride, bromide, or iodide;

with the proviso that halogen means chlorine or fluorine, and $R^3$ may contain up to twelve carbon atoms.

3. A compound of claim 2 in which X is n-propoxy, cyclopropylmethoxy, methoxycarbonylamino, i-propoxycarbonylamino, or a heteroaryl selected from 1,2,4-oxadiazol-5-yl, oxazolin-2-yl, pyrid-2-yl, pyrimidin-2-yl, pyrol-3-yl, 2H-tetrazol-5yl, 1,2,3-thiadiazol-4-yl, 1,2,4-triazol-3-yl, each optionally substituted with halogen, cyano, $C_{(1-3)}$alkyl, $C_{(1-3)}$haloalkyl, or $C_{(1-4)}$alkoxyalkyl; and $R^3$ is alkyl, $C_{(1-4)}$haloalkyl, $C_{(1-4)}$hydroxyalkyl, $C_{(1-4)}$alkoxyalkyl, $C_{(1-4)}$dialkylaminoalkyl, $C_{(1-4)}$alkylaminocarbonyloxyalkyl, $C_{(1-4)}$alkylthioalkyl, $C_{(1-4)}$alkylcaronyloxyalkyl, $C_{(1-4)}$alkoxycarbonylalkyl, carboxy$C_{(1-4)}$alkyl, benzylcarboxy, or benzoyl.

4. A compound of claim 3 in which X is n-propoxy, cyclopropyl-methoxy, pyrid-2-yl, pyrimidin-2-yl, 5-methyl-2H-tetrazol-5yl or 5-(2-fluoroethyl)-2H-tetrazol-5yl.

5. A compound of claim 4 in which $R^1$ and $R^2$ are independently selected from trifluoromethylphenyl and trifluoromethoxyphenyl.

6. The compound of claim 5 which N-(4-n-propoxyphenylmethyl)-4-[bis(4-bromophenyl) hydroxymethyl]piperidinium N-methoxy iodide.

7. The compound of claim 5 which N-(4-n-propoxyphenylmethyl)-4-5 [bis(4-trifluoromethylphenyl) hydroxymethyl]piperidinium N-ethoxycarboxylate.

8. The compound of claim 5 which N-(4-cyclopropylmethoxyphenylmethyl)-4-[bis(4-trifluoromethylphenyl)hydroxymethyl]piperidinium N-methoxycarboxylate.

9. The compound of claim 5 which N-(4-cyclopropylmethoxyphenylmethyl)-4-[bis(4-trifluoromethylphenyl)hydroxymethyl]piperidinium N-ethoxycarboxylate.

10. The compound of claim 5 which N-(4-cyclopropylmethoxyphenylmethyl)-4-[bis(4-trifluoromethylphenyl)hydroxymethyl]piperidinium N-butoxycarboxylate.

11. The compound of claim 5 which N-(4-cyclopropylmethoxyphenylphenylmethyl)piperidin-4-ylcarboxylatemethyl)-4-|bis(4-trifluoromethylphenyl) hydroxymethyl|piperidinium N-ethoxycarbonylmethoxy bromide.

12. The compound of claim 5 which N-(4-cyclopropylmethoxyphenylmethyl)-4-|bis(4-trifluoromethylphenyl)hydroxymethyl|piperidinium N-ethoxy iodide.

13. The compound of claim 5 which N-(4-cyclopropylmethoxyphenyl-methyl)-4-|bis(4-trifluoromethylphenyl)hydroxymethyl|piperidinium N-n-propoxy iodide.

14. The compound of claim 5 which N-(4-cyclopropylmethoxyphenylmethyl)-4-|bis(4-trifluoromethylphenyl)hydroxymethyl|piperidinium N-dodecoxy bromide.

15. The compound of claim 5 which N-(4-cyclopropylmethoxyphenylmethyl)-4-|bis(4-trifluoromethylphenyl)hydroxymethyl|piperidinium N-methoxy methylsulfate.

16. The compound of claim 5 which N-(4-cyclopropylmethoxyphenylmethyl)-4-|bis(4-trifluoromethylphenyl)hydroxymethyl|piperidinium N-benzoyloxy chloride.

17. The compound of claim 5 which N-(4-cyclopropylmethoxyphenylmethyl)-4-|bis(4-trifluoromethylphenyl)hydroxymethyl|piperidinium N-butoxycarboxylate.

18. The compound of claim 5 which is N-[4-(2-methyl-2H-tetrazol-5-yl)phenylmethyl]-4-[bis(4-trifluoromethoxyphenyl)hydroxymethyl]piperidinium N-methoxy chloride.

19. The compound of claim 5 which is N-[4-[2-(2-fluoroethyl)-2H-tetrazol-5-yl]phenylmethyl]-4-[bis(4-trifluoromethylphenyl)hydroxymethyl]piperidinium N-ethoxy bromide.

20. The compound of claim 5 which is N-[4-(2-(2-fluoroethyl)-2H-tetrazol-5-yl)phenylmethyl]-4-[bis(4-trifluoromethylphenyl)hydroxymethyl]piperidinium N-carboxyethoxy inner salt.

21. The compound of claim 5 which is N-[4-(2-(2-fluoroethyl)-2H-tetrazol-5-yl)phenylmethyl]-4-[bis(4-trifluoromethylphenyl)hydroxymethyl]piperidinium N-ethoxy carboxyethoxy.

22. The compound of claim 5 which is N-[4-(2-ethyl-2H-tetrazol-5-yl)-phenylmethyl]-4-[bis(4-trifluoromethylphenyl)hydroxymethyl]piperidinium N-carboxyethoxy inner salt.

23. The compound of claim 5 which is N-[4-(2-ethyl-2H-tetrazol-5-yl)-phenylmethyl]-4-[bis(4-trifluoromethylphenyl)hydroxymethyl]piperidinium N-ethoxycarbonylethoxy.

24. The compound of claim 5 which is N-[4-(2-(2-fluoroethyl)-2H-tetrazol-5-yl)phenylmethyl]-4-[bis(4-trifluoromethoxyphenyl)hydroxymethyl]-piperidinium N-ethoxycarbonylethoxy.

25. The compound of claim 5 which is N-[4-(1-methylethoxycarbonyl)phenylmethyl]-4-[bis(4-trifluoromethylphenyl)hydroxymethyl]piperidinium N-carboxyethoxy inner salt.

26. A composition containing an insecticidally effective amount of a compound of claim 1 in admixture with at least one agriculturally acceptable extender or adjuvant.

27. A method of controlling insects that comprises applying to the locus where control is desired an insecticidally effective amount of a composition of claim 26.

* * * * *